US008222015B2

(12) United States Patent
Wang et al.

(10) Patent No.: US 8,222,015 B2
(45) Date of Patent: Jul. 17, 2012

(54) HEAT RESISTANT BIOACTIVE COMPOSITION

(75) Inventors: Ping Wang, North Oaks, MN (US);
Songtao Wu, St. Paul, MN (US);
Hongfei Jia, Ann Arbor, MI (US);
Masahiko Ishii, Okazaki (JP);
Xiaodong Tong, St. Paul, MN (US);
Minjuan Zhang, Ann Arbor, MI (US)

(73) Assignees: Toyota Motor Engineering & Manufacturing North America, Inc., Erlanger, KY (US); Toyota Motor Corporation, Toyota (JP); Regents of the University of Minnesota, Minneapolis, MN (US)

( * ) Notice: Subject to any disclaimer, the term of this patent is extended or adjusted under 35 U.S.C. 154(b) by 1104 days.

(21) Appl. No.: 12/118,171

(22) Filed: May 9, 2008

(65) Prior Publication Data
US 2008/0293117 A1 Nov. 27, 2008

Related U.S. Application Data

(60) Provisional application No. 60/917,559, filed on May 11, 2007.

(51) Int. Cl.
*C12N 11/00* (2006.01)
*C12N 11/16* (2006.01)
*C12N 11/04* (2006.01)
(52) U.S. Cl. ........................................ 435/174; 435/182
(58) Field of Classification Search ........................ None
See application file for complete search history.

(56) References Cited

U.S. PATENT DOCUMENTS

| 3,622,533 | A | * | 11/1971 | O'Connor ..................... 524/195 |
| 4,540,573 | A | | 9/1985 | Neurath et al. |
| 5,134,057 | A | | 7/1992 | Kuypers et al. |
| 5,482,996 | A | | 1/1996 | Russell et al. |
| 5,989,899 | A | | 11/1999 | Bower et al. |
| 6,004,583 | A | | 12/1999 | Plate et al. |
| 6,187,842 | B1 | | 2/2001 | Kobayashi et al. |
| 6,310,105 | B1 | | 10/2001 | Damodaran |
| 6,361,797 | B1 | | 3/2002 | Kuzma et al. |
| 6,551,806 | B1 | | 4/2003 | Sturmer et al. |
| 6,596,402 | B2 | | 7/2003 | Soerens et al. |
| 6,759,220 | B1 | | 7/2004 | LeJeune et al. |
| 6,773,703 | B1 | | 8/2004 | Ettner et al. |

(Continued)

FOREIGN PATENT DOCUMENTS
EP  0952171  10/1999

OTHER PUBLICATIONS

Mozhaev et al. Biotechnology and Bioengineering, vol. XXV, pp. 1937-1945, 1983.*

(Continued)

*Primary Examiner* — Chris R Tate
*Assistant Examiner* — Douglas F White
(74) *Attorney, Agent, or Firm* — Gifford, Krass, Sprinkle, Anderson & Citkowski, P.C.

(57) ABSTRACT

A bioactive composition includes a hydrogel matrix. At least one protein is immobilized in the hydrogel matrix. The digestive protein has a half-life at least 1000 times longer than the half-life of a free digestive protein counterpart.

5 Claims, 10 Drawing Sheets

Average pore size: 100~150 nm

U.S. PATENT DOCUMENTS

| | | | |
|---|---|---|---|
| 7,048,966 B2 | 5/2006 | Thomson | |
| 2004/0115721 A1 | 6/2004 | Mao et al. | |
| 2005/0208121 A1* | 9/2005 | Barton et al. | 424/450 |
| 2006/0233747 A1* | 10/2006 | Kochendoerfer et al. | 424/85.1 |
| 2006/0281165 A1 | 12/2006 | Davis et al. | |
| 2007/0134420 A1 | 6/2007 | Koberstein et al. | |

OTHER PUBLICATIONS

Khoury et al. Biomedical Microdevices 5:1, pp. 35-45, 2003.*
Lin et al. "Hydrogels in controlled release formulations: Network design and mathematical modeling"; Advanced Drug Delivery Reviews; Sep. 22, 2006; vol. 58; pp. 1379-1408.

* cited by examiner

Average pore size:
100~150 nm

Average pore size:
< 30 nm

Estimated half lifetime:

Native glucose oxidase: 0.7 hour
Non-pretreated hydrogel glucose oxidase: ~300 days
Pretreated hydrogel glucose oxidase: ~500 days

Aging condition: bake at 110°C in a gravity convection oven

Estimated half lifetime:

Native glucose oxidase: 0.25 hour
Non-pretreated hydrogel glucose oxidase: 0.7 hour
Pretreated hydrogel glucose oxidase: 330 hour Aging condition: bake at 110°C in a gravity convection oven

Estimated half lifetime:

Native α-CT: 30 hour
Non-pretreated hydrogel α-CT: 0.1 hour
Pretreated hydrogel α-CT: 3000 hour

HEAT RESISTANT BIOACTIVE COMPOSITION

RELATED APPLICATIONS

This application claims priority of U.S. Provisional Patent Application Ser. No. 60/917,559 filed on May 11, 2007, the entire content of which is incorporated herein by reference.

FIELD OF THE INVENTION

The present invention relates to compositions and processes thereof for stabilizing bioactive materials and in particular to thermal treatments for stabilizing hydrogel-immobilized bioactive materials.

BACKGROUND OF THE INVENTION

Bioactive macromolecules such as proteins, nucleic acids, and functional enzymes have been broadly utilized in various aspects of biomedical and industrial applications. For example, nucleic acids have been used as genetic templates for polymerase chain reactions while proteins have been used in detergent mixtures to enhance digestive cleaning efficiency of the detergent.

In the detergent industry, proteins may be used as detergent additives to clean stains having a biological component. Biological stains may be present in automotive applications such as both interior and exterior surfaces of the automobile. Examples of automotive surfaces include: coatings, paints, and seat fabrics that may be contaminated when the surfaces are under prolonged exposure to bird dropping, insect debris, resins of conifer, microbes, gums, etc. Certain stains such as insect-originated stains are hard to remove with ordinary brush-free car-wash. Interior surfaces and coatings may also be easily stained with oil, protein, sugar and other ingredients in foods and beverages. Biological stains such as bird droppings, plant resins and insect body debris, when accumulated, may damage the paint surface of vehicles. Additionally, damages such as fissures or swelling associated with prolonged stain exposure may not be recoverable by heat treatment. There is therefore a need in the art for the timely removal of such stains.

In response, self-cleaning technology has been developed to reduce surface stain accumulations and make brush-free car-wash a reasonable alternative. However, traditional self-cleaning technology, known as either hydrophobic or hydrophilic coating, is only effective for the removal of inorganic dirt, but not for that of biological stains, which consist of various types of organic polymers and are often able to diffuse extensively into the sub-surface of coatings.

Proteins such as digestive proteins or enzymes are known to catalyze and decompose organic molecules. Digestive proteins may be both active and resilient in organic media, allowing various substrates to be utilized. If the substrate is insoluble or only slightly soluble in water, the maximum activity of the digestive proteins cannot be achieved in an aqueous solution. The study of digestive protein activity in non-aqueous media in the prior art is motivated principally by the need to extend the applicability of digestive proteins to the catalysis of reactions whose reactants and/or products are not water-soluble.

Although proteins such as digestive proteins or enzymes are capable of decomposing organic stain molecules they are generally not thermally stable at elevated temperatures and under dry or non aqueous conditions. There is therefore a need in the art for a thermally stable bioactive composition that may be used in elevated temperature and dry conditions. There is also a need in the art for a thermally stable bioactive composition and process for producing the bioactive composition that may be stable for various environmental stresses including elevated temperature and acidity.

SUMMARY OF THE INVENTION

In one aspect, there is disclosed a bioactive composition including a porous hydrogel matrix. At least one protein is immobilized in the porous hydrogel matrix. The protein has a half-life at least 1000 times longer than the half-life of a free digestive protein counterpart.

In another aspect, there is disclosed a bioactive composition including a hydrogel matrix pore defining a volume $V1$. At least one protein having a total volume $V2$ defined by the collective three-dimensional size of the protein is immobilized in the pore. The ratio of $(V1-V2)/V1$ is less than 20 percent.

In another aspect there is disclosed a process for stabilizing a bioactive composition including the steps of: forming hydrogel matrix pores around protein molecules; and reducing a water content within the hydrogel matrix pores while keeping the protein molecules biologically active.

DETAILED DESCRIPTION OF THE INVENTION

Figure 1:
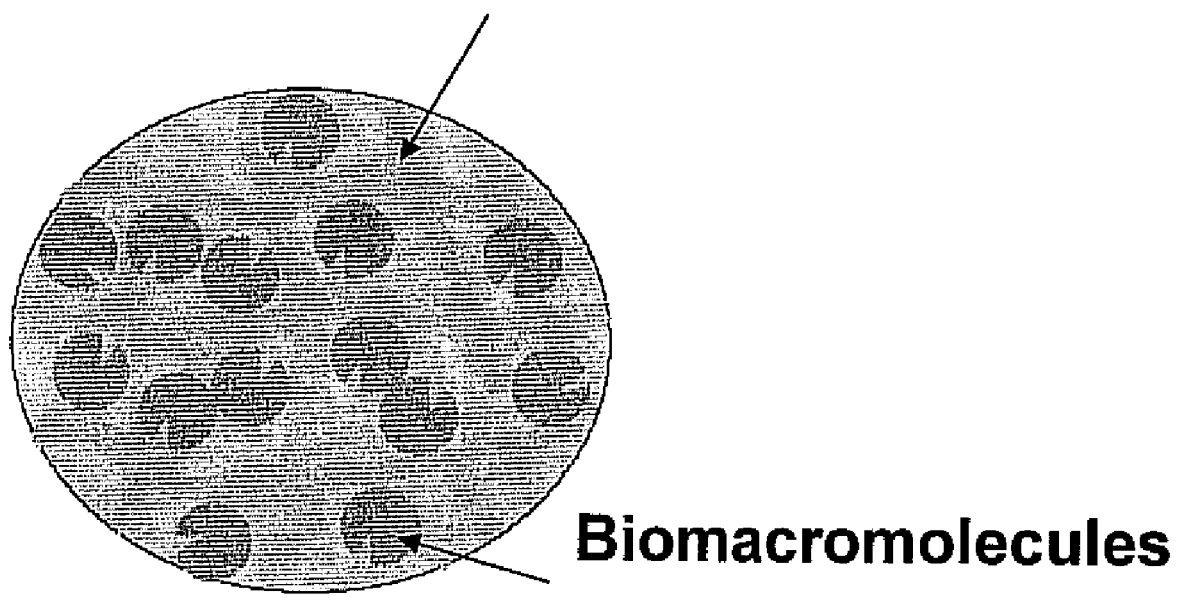
FIG. 1 is a graphical depiction of a hydrogel structure having digestive proteins entrapped within the hydrogen structure.

Bioactive macromolecules may refer to large molecules having biological functionality within a living cell. Bioactive macromolecules may include nucleic acids, digestive proteins, and functional enzymes. Other components as described below may also be included.

Proteins may act as bioactive catalysts that may selectively catalyze biochemical reactions. Various proteins may be utilized to react with biological components. The proteins may accelerate the decomposition of biopolymers or hydrolyze fats and oils. Various biological components may be reacted with the bioactive composition. For example, stains may be one biological component and may include broken bodies of bugs, animal wastes, foods, milk and other beverages, cosmetic and personal care products, as well as other biological based stains. Additional biological components other than stains may also react with the bioactive composition. Various biological components may include proteins, polysaccharides, fats or oils.

As stated above, various proteins may be utilized to react with various biological components. For example, digestive proteins such as proteases that hydrolyze protein molecules, lipases that hydrolyze lipids and fats, cellulases that hydrolyze cellulose, amylases that hydrolyze carbohydrates, as well as other digestive proteins such as peroxidases, chymotrypsin, subtilisin, superoxide dismutase, asparaginase, and cholesterol oxidase may be a component of the bioactive composition.

Various analytical assays and diagnostic techniques may be utilized to quantify the activities of bioactive coatings. The loading of a digestive protein within a composition may be estimated based on calorimic assays and mass balance calculations. Various distributions of digestive proteins in a composition or coating may be verified using fluorescence microscopy. The thermal stability of a digestive protein in a bioactive coating may be evaluated by aging the coatings in an air-heat oven while monitoring the activity change.

The protein-based bioactive composition should remain functional in dry or semi-dry environments. In general protein-based systems may include water or other aqueous elements to allow the reaction of the protein and a biological component to take place. Additionally, a protein-based bioactive composition according to another aspect should be stable and retain its bioactivity in various harsh conditions. Harsh conditions may include elevated temperatures, acidic conditions, mechanical shearing, exposure to ultraviolet radiation, as well as other environmental conditions. The protein-based bioactive composition should not denature and remain bioactive under such conditions.

In one aspect, the bioactive composition may include proteins dispersed into a solid porous material including a hydrogel that is formed through the polymerization between monomers and crosslinkers. Various monomers may be utilized and include hydrocarbons such as alkene and arene materials. Various monomers include phenylethene, ethane, acrylic monomers such as acrylic acid, methyl methacrylate, and acrylamide, as well as other monomers such as vinyl alcohol and vinyl pyrrolidone. Various crosslinkers may also be utilized and include N,N'-methylenebisacrylamide, polyazonium compounds, and glutardialdehyde. Various polymerization initiators may be utilized and include ammonium persulfate and tetramethylethylenediamine (TEMED). During the polymerization reaction, the monomers and crosslinkers may form a hydrogel matrix that includes matrix pores.

In one aspect, the proteins may be entrained or positioned within the hydrogel matrix pores. The hydrogel matrix pores may have various sizes that may receive from one to ten proteins and even more preferably from one to two proteins. The concentration of bioactive macromolecules present in the hydrogel matrix may be varied for various applications. In one aspect, the bioactive macromolecules such as proteins may be present in a level of from 0.05 to 7.0 dry weight percent, and preferably 0.07 to 6.0 dry weight percent, and even more preferably 0.1 to 5.0 dry weight percent. The hydrogel matrix pores are sized such that they allow diffusion of biological components into the hydrogel matrix such that the proteins may act upon them. In this manner, the proteins remain positioned within the hydrogel matrix pores and remain biologically active to react with various biological components. The hydrogel matrix prevents the denaturing of the proteins and increases the half-life of the proteins at least 1,000 times greater than the half-life of free digestive proteins.

Figure 2:
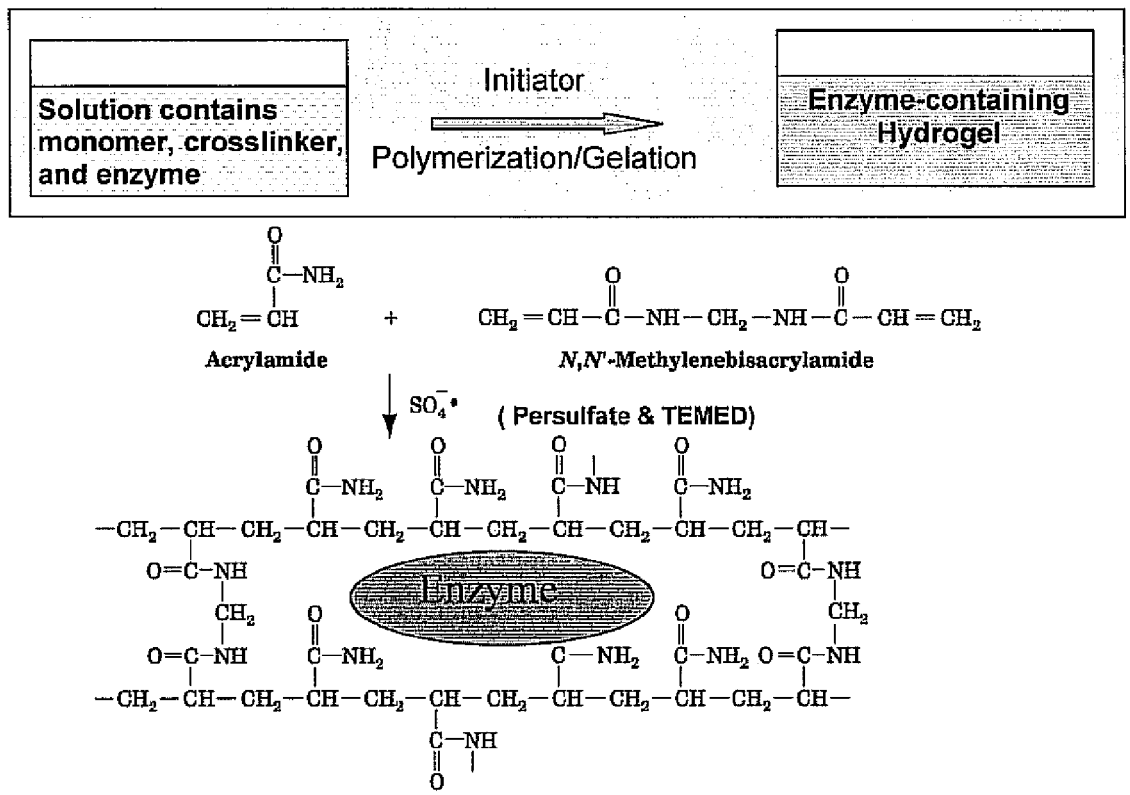
FIG. 2 is a graphical depiction of the formation of a hydrogel structure with a digestive protein entrapped within the hydrogel structure for an acrylamide monomer, N,N'-methylenebisacrylamide crosslinking compound and a polymerization initiator of ammonium persulfate and tetramethylene diamine.

Referring to FIG. 1 there is shown a schematic representation of a protein-hydrogel structure that includes the pores having at least one protein positioned within the pore. In one example, and as shown in FIG. 2, a polymerization reaction between an acrylamide and N,N'-methylenebisacrylamide will form a hydrogel matrix such that proteins are housed and protected within a pore of the hydrogel structure.

Various additives may be included in the protein-hydrogel structure including surfactants, various crosslinking compounds, additional biological compositions, and various other biologically active agents, therapeutic agents, and other additives. Additionally, the hydrogel may be formed on a surface that is coated by centrifugal force with a solution that contains a hydrogel forming monomer, a protein, and a crosslinking agent including polyazonium compound and glutardialdehyde. Various polyazonium compounds may be utilized and may include monomeric or polymeric organic compounds having at least two side chains and/or a terminal diazonium salt group. Various polyazonium compounds include benzidine-tetrazonium salt such as benzidinetetrazonium chloride-zinc chloride double salt, a diethylbenzidinetetrazonium salt such as diethylbenzidinetetrazonium chloride-zinc chloride double salt or diethylbenzidinetetrazonium sulfate, a dichlorobenzidinetetrazonium salt such as dichlorobenzidinetetrazonium chloride-zinc chloride double salt, an n-tolidinetetrazonium salt such as o-tolidinetetrazonium chloride-zinc chloride double salt or o-tolidinetetrazonium sulfate, an o-dianisidine-tetrazonium salt such as o-dianisidinetetrazonium chloride-zinc chloride double salt.

Various surfactants may include surface active agents that reduce the surface tension of a liquid. Various surfactants may be utilized to control the hydrogel properties and morphology as well as enhance the activity of the proteins. Various surfactants include lauryl sulfate and octyl sulfate as anionic surfactants; cetylpyridinium chloride and dodecyltrimethylammonium bromide as cationic surfactants; and pluronic F-68 and Tween 20 as non-ionic surfactants.

In one aspect, a surfactant may be added from between 0.5 to 5.0 weight percent of an aqueous component of the hydrogel forming solution. When the polymer component of the hydrogel solution is polyurethane, urethane prepolymers may be mixed with water along with one or more types of proteins, surfactant, and buffer salts.

In one aspect, the bioactive composition may include bioactive macromolecules such as proteins that are added as a freeze-dried powder or aqueous solution. In one aspect, the bioactive composition may include at least one of an oxidoreductase, a transferase, a hydrolase, a lyase, an isomerase, a ligase, a protease, an amylase, a cellulase, a lipase, a peroxidase, a tyrosinase, a glycosidase, a nuclease, an aldolase, a phosphatase, a sulfatase, or a dehydrogenase.

The bioactive composition may optionally include at least one biochemically active agent which illustratively includes an antibody, a nucleic acid, a fatty acid, a hormone, a vitamin, a mineral, a structural protein, an enzyme such as glucose oxidase and alcoholase, a therapeutic agent such as a histamine blocker, and an anti-thrombogenic material such as heparin.

Additional therapeutic agents illustratively include cardiovascular drugs such as cardioactive and casoactive drugs, blood pressure increasing agents, antihypertensive agents, antiarrhythmic drugs, beta blockers, cardiac glycosides, synthetic ardiotonic drugs, calcium antagonists, drugs affecting circulation, blood diuretics; neuropharmaceuticals such as neuropharmaceutical agents, analeptics, analgesics, antipyretics, anesthetics, appetite suppressants, antiepileptic drugs, sedatives, local anesthetics, Parkinsonism treatment, antipsychotics, neuroleptics, skeletal muscle relaxants, spasmolytics; gastrointestinal drugs such as anti-ulcer drugs, antiemetics, laxatives, gastroprokinetic agents, motilin; respiratory tract drugs such as cough remedies, antiasthmatics, antiallergics; anti-infective drugs such as antibiotics, synthetic chemotherapeutic agents, antimycotics, anthelmintics, HIV therapeutics; endocrine drugs such as steroids, peptide hormones, chemical contraceptives, thyrotherapeutics, oral antidiabetic drugs; and miscellaneous drugs such as gout remedies, immunotherapy, cancer chemotherapy, ophthalmological agents.

In one aspect, the hydrogel including the protein may be subjected to a heat treatment to form a hydrogel protein structure providing increased stability for the protein macromolecule. As stated above, denaturization of bioactive macromolecules such as proteins and nucleic acids results in a change in their structure. Various external stresses including acidic, basic, inorganic salts or organic solvents and heat may cause the denaturization of the proteins. The denaturization of the proteins may result in various problems including loss of solubility of communal aggregation, formation of condensation, as well as disruption of tertiary structural integrity and loss of functionality of the biological components.

The hydrogel protein composition defined above includes a bioactive macromolecule such as a digestive protein or nucleic acid positioned within a pore defined by the monomer crosslinkage and polymerization. The bioactive molecule is thereby immobilized within the pore, as defined above. However, a portion of a hydrogel composition may be water. Within the hydrogel, water freely floats within and amongst the pores defined by the polymer chain lattice such that the immobilization of the biological macromolecule may be dependent upon its molecular weight relative to the size of the pore, the water content, and the mobility of the water component within the hydrogel. In one aspect, as the water content or water mobility increases the biological macromolecule may be able to move with the water to a neighboring pore within the confinement of the hydrogel matrix polymers. Such movement may result in the formation of macromolecule aggregates resulting in an uneven distribution of the biological macromolecule. Additionally, a protein may lose tertiary structure and become denatured when the protein is free and unbound as opposed to when it is partially confined or bound. Therefore, the stability of the biological macromolecules may be improved through the porosity control of the resultant hydrogel through the manipulation of the water content of the hydrogel such as removing the free water located within the hydrogel.

Additionally, various other techniques may be utilized to regulate the porosity or solidification of a polymeric material including selection of the chemical composition, molecular weight and availability of various groups for crosslinking as well as the degree of crosslinking of the various polymers. Additionally, various other factors such as the ionic strength, osmolarity and pH of the polymer solutions, as well as addition of various viscosity modifying agents such as sorbitol, glycerin or sucrose as well as other materials such as lipids or highly charged polymers may alter the surface binding of macromolecules that are encapsulated within the hydrogel pores. In one aspect, a thermal pretreatment procedure may be utilized such that the functionality and viability of the immobilized biological macromolecules is maintained while the stability of the biological macromolecule is improved.

Figure 3:
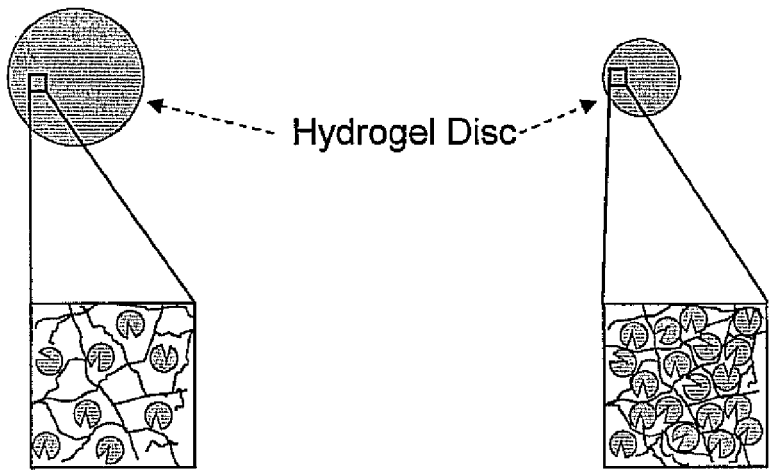
FIG. 3 is a diagram of a hydrogel porosity change after thermal treatment.

In one aspect, a thermal pretreatment may include a heat-assisted procedure to remove water from the hydrogel. Various factors including the degree of temperature, the period of time for heat treatment, the starting water content of the hydrogel, as well as the molecular weight of the targeted bioactive macromolecules will have a result on the stability of a hydrogel matrix, Referring to FIG. 3, there is shown a hydrogel specimen in the form of a disc having macromolecules of a biological agent entrained within the pores but having a degree of freedom to move about within the pores. As water is removed from the hydrogel matrix the pores become smaller in dimension such that the biological macromolecules are in a more compact arrangement with little or no degree of movement. As such, the structural denaturization or functional inactivation of the biological macromolecules is reduced.

Figure 5A:
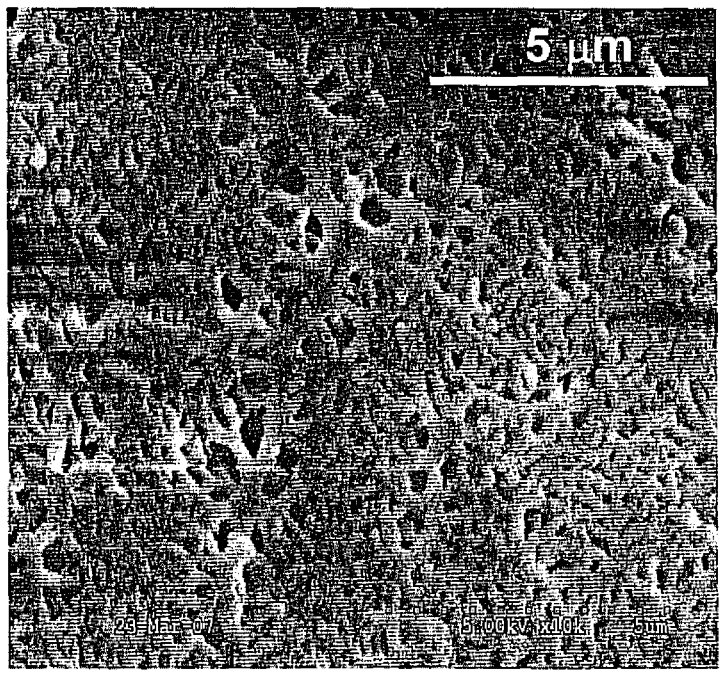
FIGS. 5A and 5B are scanning electron microscope (SEM) scans detailing the porosity of a hydrogel-entrapped glucose oxidase before and after thermal pretreatment, respectively.
Figure 5B:
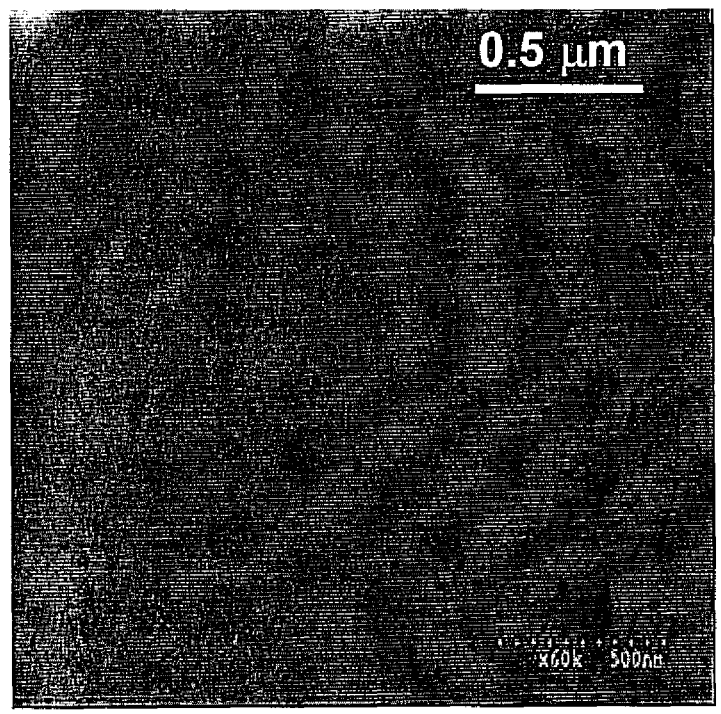

Referring to FIGS. 5A and B there are shown SEM micrographs of a hydrogel having a hydrogel before a heat-assisted water removal as shown in FIG. 5A and after thermal pretreatment as shown in FIG. 5B. As can be seen in the figures, the untreated hydrogel has pore sizes of from about 100 to 150 nanometers whereas the thermally pretreated hydrogel matrix is condensed such that the pore sizes are approximately less than 30 nanometers.

In one aspect, an initial hydrogel is provided such that it has from 55 to 95 weight percent of water and 0.01 to 5.0 dry weight percent of bioactive macromolecules. A thermal pretreatment may be performed on the hydrogel material depending upon the starting water content and the particular type of the bioactive macromolecule. For example, a hydrogel specimen having a glucose oxidase may be pretreated at temperatures of from 20 to 110 degrees Celsius for time periods of from 24 hours to 7 days in length. A hydrogel specimen having α-chymotrypsin may be pretreated at temperatures of from 20 to 55 degrees Celsius for time periods of from 24 hours to 7 days in length. When water is removed from the hydrogel matrix, pore sizes are reduced and the entrained bioactive macromolecules become more stabilized.

In one aspect the thermal pretreatment may be defined in terms of a percentage of weight change before and after the thermal pretreatment. A hydrogel has a starting weight of $W1$ and a resultant weight of $W2$ after a thermal pretreatment. The Length of a heating step is targeted such that the percentage of weight change as formulated by $(W1-W2)/W1$ is a value greater than 20 percent, preferably greater than 30 percent, and more preferably greater than 50 percent.

Additionally, the hydrogel composition before and after thermal treatment may be defined by the volume of the matrix pore V1 before thermal pretreatment and one or more bioactive macromolecules that are housed within the pore and have a total volume V2 defined by the three-dimensional size of the bioactive macromolecules. The difference between volume V1 and volume V2 may be accessible by water molecules. As water molecules are removed during the thermal pretreatment the ratio of (V1−V2)/V1 changes. In one aspect, the ratio of (V1−V2)/V1 is less than 30 percent, preferably less than 20 percent, and more preferably less than 10 percent.

In another aspect, a hydrogel composition may include a hydrogel matrix having a water content and a plurality of bioactive macromolecules disposed within pores of the hydrogel matrix. The water content may be less than 10 percent of the hydrogel matrix, preferably less than 5 weight percent of the hydrogel matrix.

In another aspect, a thermal pretreatment may be utilized on a hydrogel that has been previously thermally pretreated but has been exposed to a wet application in aqueous solutions. The reconditioning thermal pretreatment may be defined in terms of a first hydrogel specimen that has an initial net weight W1, an initial dry weight W2 after thermal pretreatment as described above, and a net weight W3 after an aqueous application, and a reconditioned dry weight W4 after another application of a thermal pretreatment. The weight change ratio of (W1−W4)/W1 may be at least 70 percent of the weight change ratio of (W1−W2)/W1 such that the hydrogel may be refurbished.

The composition of a hydrogel matrix and biological macromolecule may also be described in terms of the half-life of the macromolecule relative to either native counterparts that are not within a hydrogel matrix or in terms of a macromolecule within a hydrogel that has not been thermally treated. The half-life of a biological macromolecule may be calculated by applying kinetics of thermal inactivation and is defined as the time for the biological activity of the macromolecules to decay to half of its initial value. Calculations associated with the half-life of a macromolecule are provided in Example 4. As will be discussed in more detail in the Examples section, the half-life of various biological macromolecules when exposed to external stresses such as elevated temperatures demonstrate an improved half-life in comparison to nonprotective macromolecules that are rendered denatured rapidly when exposed to elevated temperatures such as 80° Celsius. Additionally, and as described in the Examples section, the thermal pretreatment in conjunction with the immobilization of a biological macromolecule with the hydrogel may result in increase of half-life of the macromolecules in comparison to nonprotected biological macromolecules.

EXAMPLES

Example 1

Entrapment of Glucose Oxidase (GOx) into Polyacrylamide Hydrogel

An exemplary protein, glucose oxidase (GOx, 5 mg) is dissolved in 2 ml of 0.1M pH 7.0 sodium phosphate buffer, and then mixed with 1.2 ml of deionized water, 100 μl ammonium persulfate (10% w/v in DI water) and 6.8 ml of 30% acylamide/bis solution (purchased from Bio-Rad Laboratories). Hydrogel polymerization is initiated with the addition of 4 μl of NNN'N'-tetramethyleethylenediamine (TEMED) at room temperature. The hydrogel solution is added carefully into a glass enclosure (8.3×7×0.075 cm³) using the pipette and kept for at least 4 hours to allow the polymerization to complete. The protein containing hydrogel is punched into small discs with a diameter of 16.2 mm, which are rinsed and dried for further use.

Example 2

Activity Assays for Native and Hydrogel-Entrapped Glucose Oxidase (GOx)

Activities of native or hydrogel-entrapped GOx are measured by using a two-coupled reaction at the room temperature:

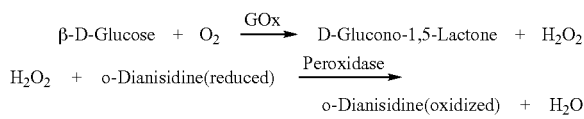

GOx catalyzes the oxidation of β-D-glucose, which produces gluconolactone and $H_2O_2$. $H_2O_2$ further reacts with o-dianisidine (reduced form) and releases a product (oxidized o-dianisidine) that is monitored on a spectrophotometer at a wavelength of 500 nm. Reduced o-dianisidine, in the presence of peroxidase, will transform to the oxidized counterpart, producing a color that is measured at 500 nm by Cary 50 Spectrometer.

To measure the native GOx, a reaction mixture (1.1 ml) contains 0.1 mol glucose, 7 μg horseradish peroxidase, 0.17 mM O-dianisidine, and 35 μl enzyme (0.4-0.8 unit/ml) in 50 mM pH 5.1 Sodium Acetate Buffer. On the other hand, to measure the activity of hydrogel-entrapped glucose oxidase, the dried hydrogel disc is immersed into deionized water for at least 2 hours to reach a fully swollen state before the activity test. Each hydrogel disc is added to 20.7 ml of 0.1M glucose solution containing 0.14 mg horseradish peroxidase and 1.1 mg O-dianisidine. The reaction with hydrogel-entrapped GOx is conducted in 20-ml vials. Aliquots of 1 ml each are taken periodically and recombined immediately after measuring the product concentration using UV absorbance at 500 nm.

Comparisons are made based on a residual activity reading which is calculated by the formula: $A_n/A_m$ whereas $A_m$ stands for activity at a first time-point, $A_n$ stands for activity at a second or later time-point.

Example 3

Increased Thermal Stability Observed with Glucose Oxidase (GOx) Entrapped in Polyacrylamide Hydrogel Improved thermal stability is observed in the case of entrapped GOx in comparison to free GOx. The analysis of thermal stability is carried out in a temperature-controlled oven. The hydrogel-protein discs are incubated at 80° Celsius for various times and their residual activities are measured following the protocol described in Example 5. The stability of native dry protein is also tested as control.

Example 4

Calculation of Half-Life of Both the Freely Unbound Macromolecules and those Entrapped Via Hydrogel Matrix Half-life time $t_{1/2}$ is calculated from experimental data by applying the kinetics of thermal inactivation and is defined as the time for the activity of a bioactive macromolecule to decay to half of its initial value.

Different formulas and simulation methods are applied to freely unbound macromolecules and to those macromolecules that are previously hydrogel-entrapped. The thermal inactivation of native enzyme is assumed to obey the classical first-order deactivation mechanism:

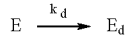

whereas E is the active enzyme state, $E_d$ represents the totally inactivated enzyme, and $k_d$ is the first-order inactivation rate constant. The expression for enzymatic activity is derived analytically, and is resolved for the kinetic parameters. Thus, the time-dependent loss in activity is expressed as below, $$A_t/A_0 = e^{-k_d t}$$

whereas $A_t$ is the residue activity at time=t, and $A_0$ is the initial activity at time=0. The resultant $A_t$ and $A_0$ are the measurable components in the experiments. Therein, the least square method was used to obtain the stimulated value of $k_d$. Therefore, the half-life $t_{1/2}$ for native enzyme is defined and calculated from the following equation:

$$t_{1/2} = \ln 0.5/(-k_d)$$

The hydrogel-entrapped enzyme would follow a non-first order deactivation mechanism, which factors in the impact of the hydrogel-assisted entrapment. Assuming the existence of an intermediate enzymatic state, $E_1$, with a reduced activity, $\alpha_1$, and a deactivated form of enzyme ($E_2$) with a reduced activity, $\alpha_2$, $k_1$ and $k_2$ were rate constants of different steps:

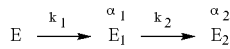

Thus, the above equation is transformed to be $$A = A_0 \left\{ \left[ 1 + \left( \frac{\alpha_1 k_1 - \alpha_2 k_2}{k_2 - k_1} \right) \right] \exp(-k_1 t) - (\alpha_1 k_1 - \alpha_2 k_1)/(k_2 - k_1) \exp(-k_2 t) + \alpha_2 \right\}$$

Substituting the experimental values of A and $A_0$ to the above equation, the computer software Matlab program is used to solve the non-linear equation matrix to obtain the related parameter values $\alpha_1$, $\alpha_2$, $k_1$ and $k_2$. Thus, half-life is simulated and obtained when $A/A_0$ is equal to be 0.5

Figure 6:
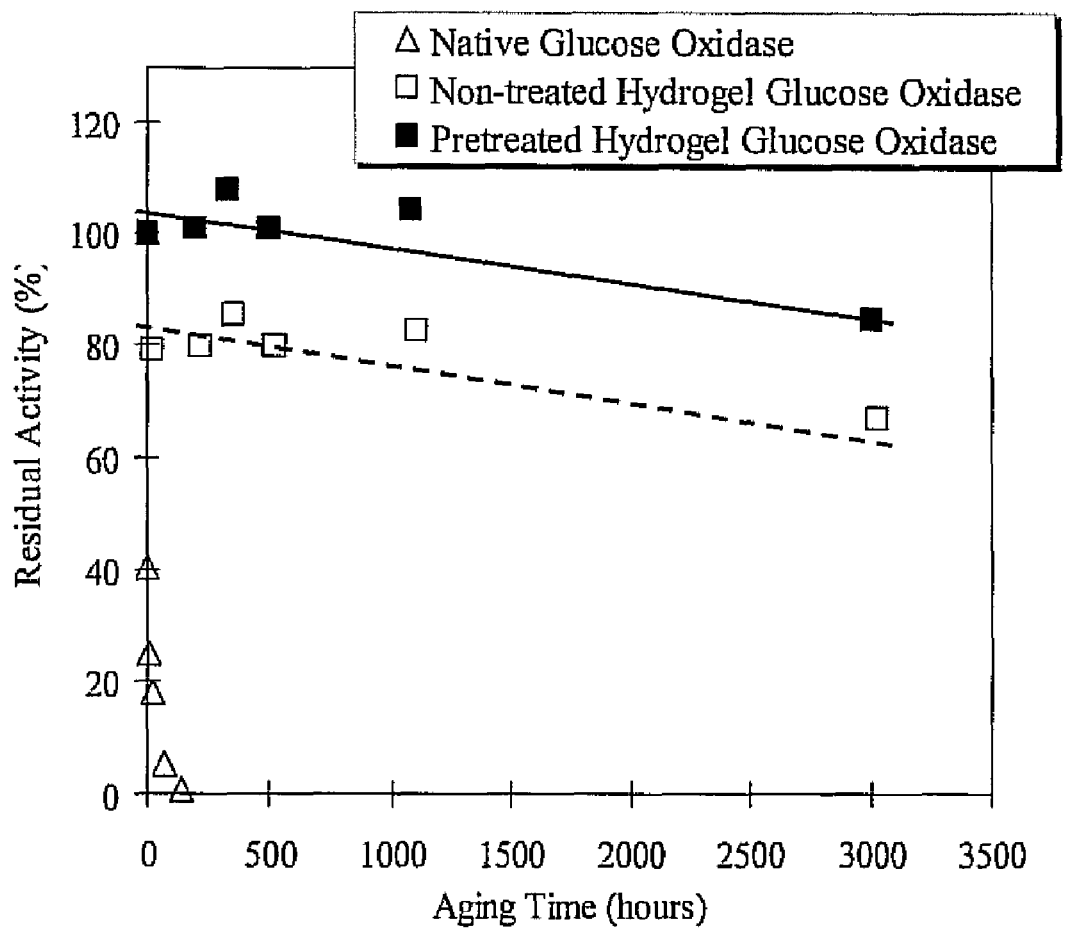
FIG. 6 is a figure of the relative activity as a function of time at 80° Celsius for thermal pretreated hydrogel-entrapped glucose oxidase molecules, non-thermal pretreated hydrogel-entrapped counterparts, and freely unbound native counterparts.
Figure 7:
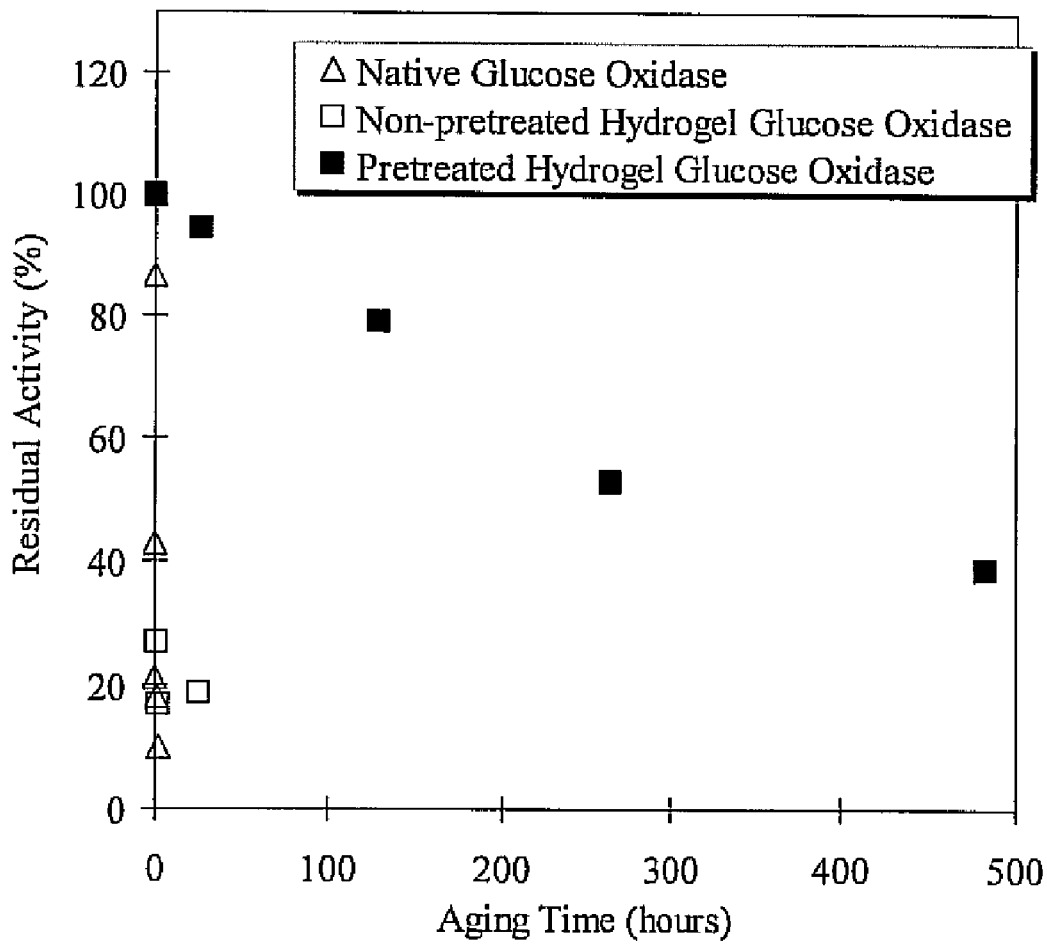
FIG. 7 is a figure of the relative activity as a function of time at 110° Celsius for thermal pretreated hydrogel-entrapped glucose oxidase molecules, non-thermal pretreated hydrogel-entrapped counterparts, and freely unbound native counterparts.

Referring to FIG. 6, there is shown a plot of a hydrogel entrapped GOx protein. The hydrogel entrapped GOx displayed no aggregation using fluorescence microscopy, indicating an improved dispersion. As shown in the figure, the thermal stability of the hydrogel entrapped GOx is surprisingly high. In the test, less than about 20% of activity reduction is observed after 3000 hrs of aging at 80° C. Based on the extrapolation of test's results, the half lifetime is estimated as approximately 500 days. The half life is a significant increase in comparison to the half life of less than one hour for free digestive protein. The increase is approximately 12,000 times of the free digestive protein.

Example 5

Entrapment of α-Chymotrypsin (α-CT) into Polyacrylamide Hydrogel

The entrapment of α-CT into polyacrylamide hydrogel is performed as the following procedure: 0.5-10 milligram of α-CT is added to 0.42 ml of 0.01 M pH 7.5 sodium acetate buffer; the buffer mixture is then mixed with 9.33 ml of 30% acylamide/bis solution and 0.25 ml of DI $H_2O$ to make a 10 ml of solution with total monomers concentration T=28% and cross-linker concentration C=5%. The polymerization is initiated in a glass enclosure (8.3×7×0.075 cm³) by adding 100 μl fresh prepared ammonium persulfate (10% w/v in deionized water) and 4 μl of TEMED at room temperature. At least 4 hours is needed for complete gelling to entrap enzyme in the hydrogel. The resulting hydrogel plates from the glass enclosures are punched into small discs with a diameter of 16 mm for further tests.

Example 6

Activity Assays for Native and Hydrogel-Entrapped α-Chymotrypsin (α-CT)

For native enzyme, 50 μl of enzyme solution (1 mg/ml) is mixed with 2.44 ml of sodium acetate buffer and 13 μl of 160 mM SAAPPN (N-succinyl-Ala-Ala-Pro-Phe-p-NitroAnilide) stock solution in a cuvette. Reaction activities are determined by monitoring the absorbance at 410 nm.

For hydrogel-entrapped α-CT, the dried gel disc is immersed into deionized water for at least 2 hours to reach a fully swollen state before activity test. Each reaction vial of 20 milliter contains 4.975 ml of pH 7.5, 10 mM sodium acetate buffer with 5 mM calcium acetate and 25 μl of 160 mM SAAPPN stock. The reaction is initiated by the addition of hydrogel-entrapped enzyme with stirring at 200 rpm. Aliquots of 1 ml each are taken periodically and recombined immediately after measuring the product concentration using UV absorbance at 410 nm.

Example 7

Non-Leakage Demonstration Regarding the Hydrogel-Entrapped Digestive Proteins

Figure 11:
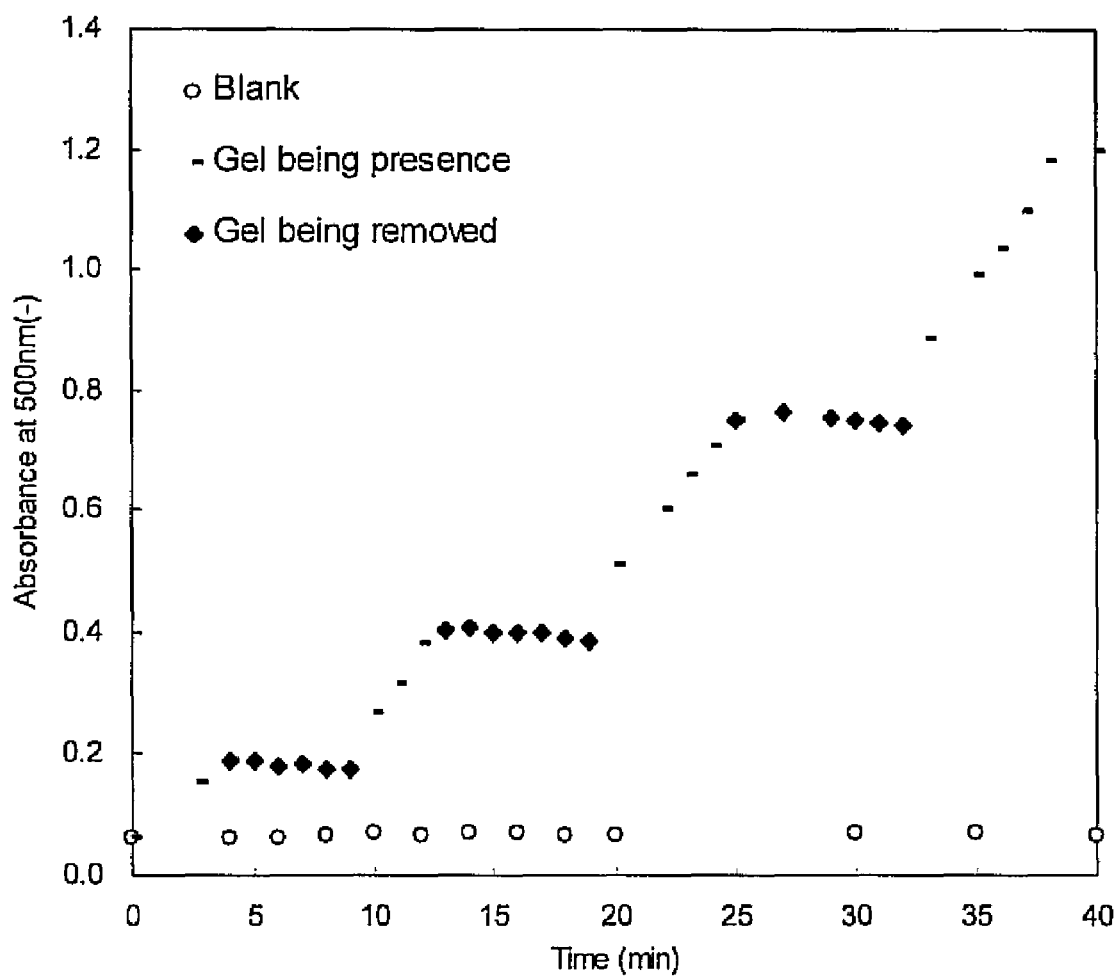
FIG. 11 is a plot of the absorbance as a function of time at 500 nm with or without the presence of a hydrogel-entrapped glucose oxidase disc for an activity assay reaction mixture.

During the activity testing described in Examples 4 and 6, the submerged hydrogel disc is taken out of the reaction mixture for several minutes and then is re-immersed back into the respective reaction vial. This step may be repeated for several times during the activity assay period. The absorbance of the reaction mixture immediately after each withdrawal of the hydrogel disc is measured by UV-Vis at 500 nm for hydrogel-entrapped GOx and at 410 nm for hydrogel-entrapped α-CT. As seen from FIG. 11, no significant increase in light absorption is observed after each withdrawal. This observation indicates that there is no appreciable protein leakage from the discs to the reaction solutions during the activity assays.

Example 8

Thermal Pre-Treatment of the Hydrogel-Entrapped Bioactive Macromolecules

Hydrogel-entrapped glucose oxidase (GOx) and α-chymotrypsin were prepared as shown in Examples 1 and 5. For the purpose of investigational comparisons, the resultant hydrogel discs were subject to the following illustrated treatments.

Figure 4:
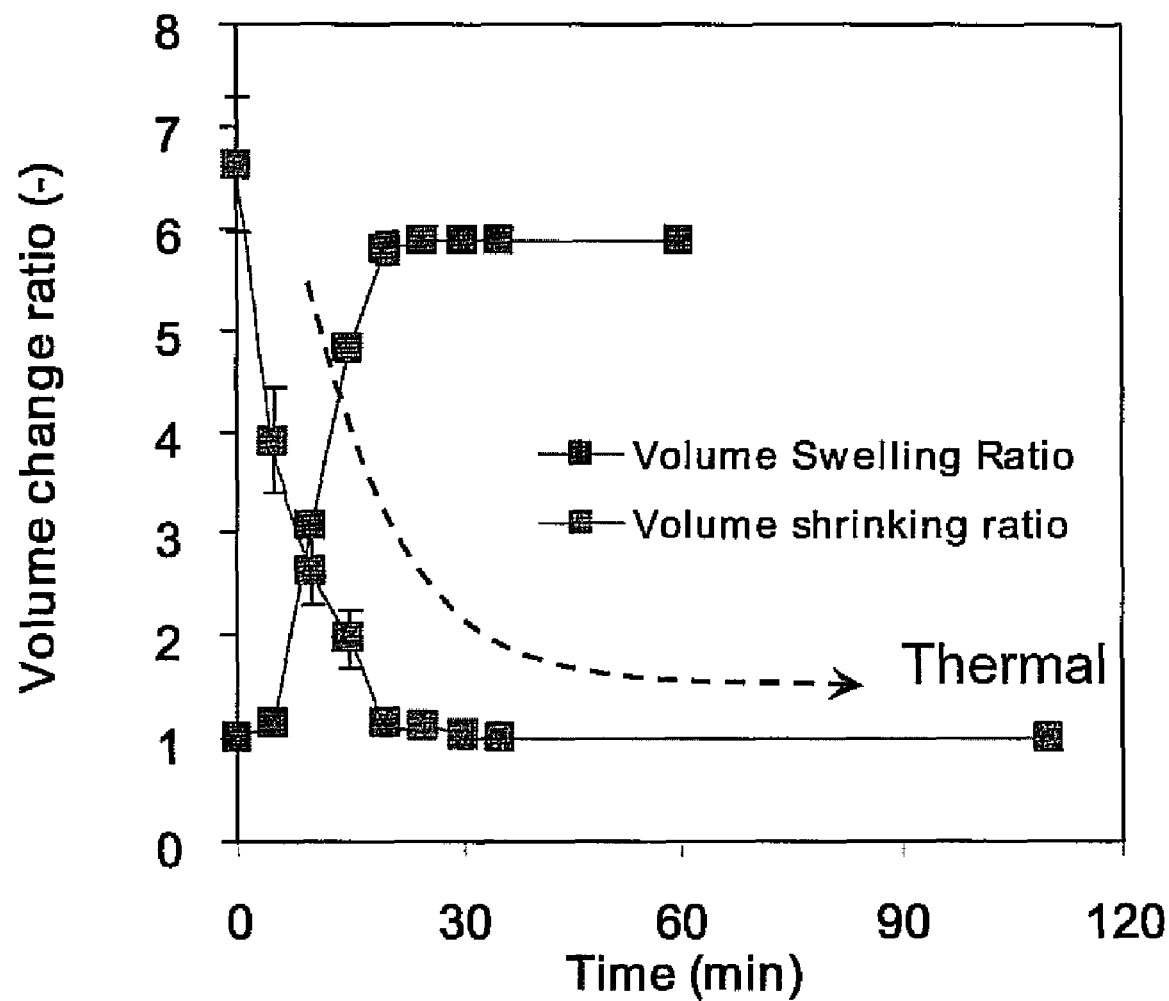
FIG. 4 is a figure detailing the volume change ratio of hydrogel-entrapped glucose oxidase material after thermal pretreatment and rewetting in water.

Incubation in an oven under specific temperatures—For hydrogel-entrapped glucose oxidase, an effective pre-treatment temperature is illustratively in the range from 20 degree Celsius to 80 degree Celsius. A fresh hydrogel disc was placed into a petri dish and incubated in the oven at 80 degree Celsius for 24 hours. Then the resultant dry hydrogel disc was removed for further tests. As shown in FIG. 4, acrylamide hydrogel matrix containing 84 weight percent of water and 0.2 dry weight percent of the entrapped glucose oxidase is subject to an inventive thermal pretreatment in an oven of 80 degree Celsius for the time period indicated on the graph. The volume shrinking ratio is defined as percentage of weight changes due to water removal. The volume swelling ratio is defined as percentage of weight changes upon a re-wetted hydrogel matrix that has been previously thermal pretreated. Each data point represents an average of four replicates. As shown in FIG. 4, water removal occurs rapidly in the first 30 minutes and significantly tapers off thereafter. This observation is consistent with the understanding that there is a large amount of free water in the hydrogel matrix that gets vaporized quickly upon the imposition of heat. An extended heat treatment after the first 30 minutes removes residual water molecules that are left embedded amongst the hydrogel polymers.

For hydrogel-entrapped α-chymotrypsin, the effective oven temperature was in the range from 20 degree Celsius to 55 degree Celsius. A fresh hydrogel disc was incubated in the oven at 55 degrees Celsius for 24 hours and the resultant dry hydrogel disc was removed for further tests.

FIG. 6 is a plot of the relative activity of the thermal pretreated hydrogel-entrapped glucose oxidase in an oven of 80 degree Celsius for an extended period of time. The estimated half-life of the thermal pretreated glucose oxidase molecules is greater than 500 days compared to minutes for the freely unbound native counterparts.

Figure 8:
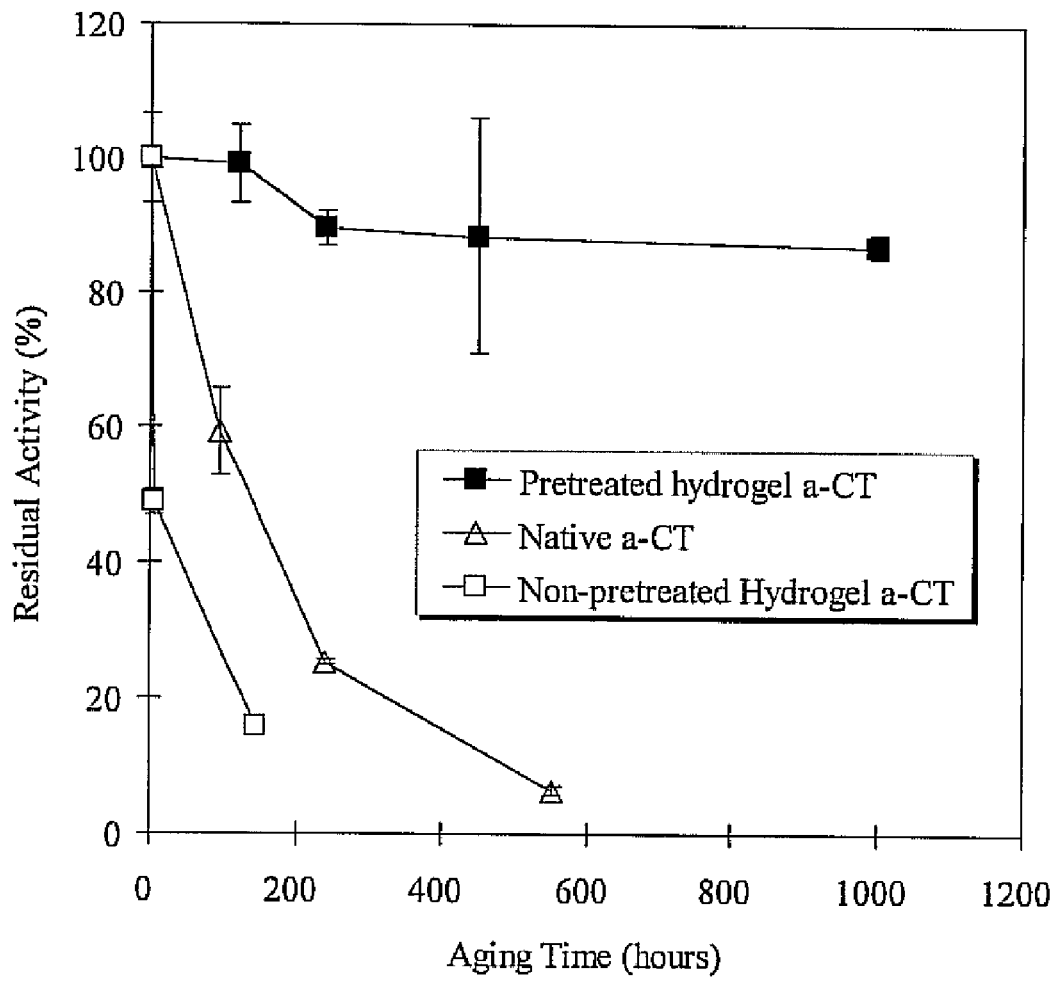
FIG. 8 is a figure detailing the relative activity as a function of time for thermal pretreated hydrogel-entrapped α-chymotrypsin molecules, non-thermal pretreated hydrogel-entrapped counterparts, and freely unbound native counterparts.

FIG. 8 is a plot of the relative activity of the thermal pretreated hydrogel entrapped a-Chymotrypsin in an oven of 80 degree Celsius for an extended period of time. The estimated half-life of the thermal pretreated α-Chymotrypsin molecules is about 700 days compared to 125 hours for the freely unbound native counterparts.

Figure 9:
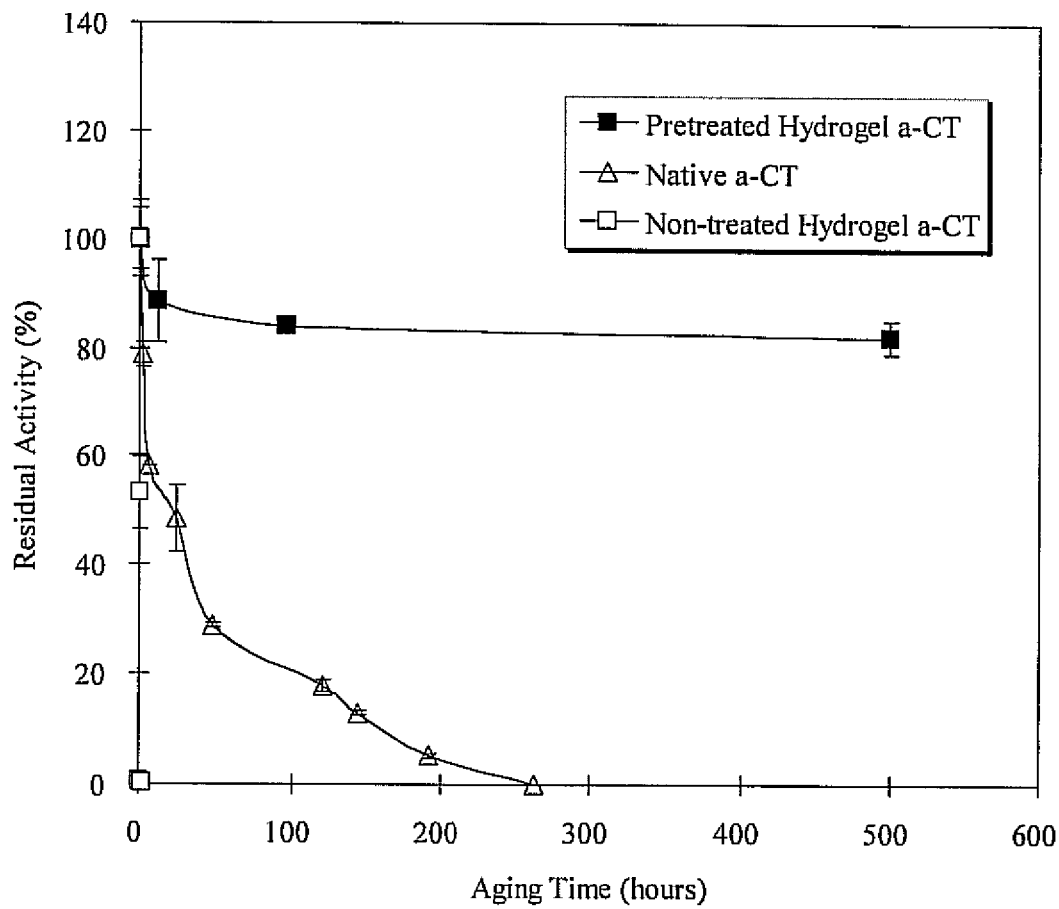
FIG. 9 is a figure of the relative activity as a function of time at 110° Celsius for thermal pretreated hydrogel-entrapped α-chymotrypsin molecules, non-thermal pretreated hydrogel-entrapped counterparts, and freely unbound native counterparts.

FIG. 9 is a plot of the relative activity of the thermal pretreated hydrogel entrapped α-Chymotrypsin in an oven at 110 degree Celsius for an extended period of time. The estimated half-life of the thermal pretreated α-Chymotrypsin molecules is about 1 year compared to about 1 day for the freely unbound native counterparts.

Example 9

Stability of Thermal Pretreated Hydrogel-Entrapped Glucose Oxidase (GOx) Under a Combined Harsh Condition Hydrogel discs containing bioactive macromolecules such as GOx were prepared as shown above in Example 1 and thermal treated as shown in Example 3. Stability was investigated under a combined harsh condition including a combination of high temperature and polar solvent. Illustratively, the pretreated hydrogel discs are incubated in 10 ml of pure ethanol. After soaking in ethanol for up to an hour, these discs were then placed into an oven at a temperature of 75 degrees Celsius. The discs were periodically removed from the oven chamber for activity determination.

Figure 10:
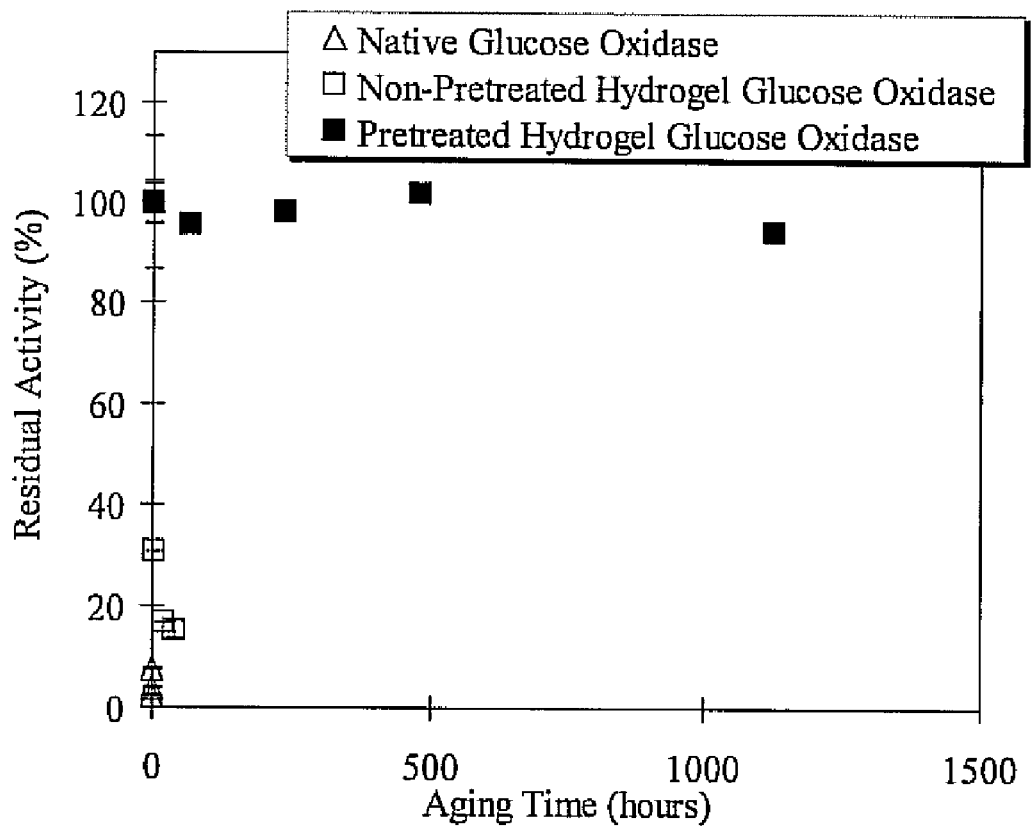
FIG. 10 is a plot of the relative activity as a function of time in a combined harsh condition experiment for a thermal pretreated hydrogel-entrapped glucose oxidase, a non-thermal pretreated hydrogel-entrapped counterpart, and a freely unbound native counterpart.

As shown in FIG. 10, the combined harsh condition of dry heat of 75 degrees Celsius and the presence of ethanol elicits no significant effect on the thermal preheated GOx over an examined period of 1200 hours compared to the native GOx counterpart that gets denatured and inactivated instantaneously within a matter of minutes. The thermal pretreated GOx data in the figure is extrapolated to indicate a half-life of approximately 4,500 hours under the combined harsh conditions.

Example 10

Stability of Pretreated Hydrogel-Entrapped GOx Under UV Light

Hydrogel-entrapped GOx discs were prepared according to Example 1 and thermal pretreated according to Example 3. After pretreatment, the stability of hydrogel-entrapped GOx was investigated under V light. Illustratively, the pretreated hydrogel discs were irradiated with a 365 nm long wave lamp (8 watts, UVL-18, UVP, Upland, Calif., USA) for 12 hours. Then the hydrogel discs were removed after UV radiation for activity assay to determine residue activities. No appreciable activity loss was found before and after the UV radiation for the thermal pretreated hydrogel-entrapped GOx.

The invention claimed is:

1. A bioactive composition comprising:
   a porous hydrogel matrix;
   an effective amount of at least one digestive protein immobilized in the porous hydrogel matrix, wherein the hydrogel matrix pore defines a volume V1; and the at least one digestive protein has a total volume V2 defined by the collective three-dimensional size of the protein wherein the ratio of (V1–V2)/V1 is less than 20 percent, the protein having a half-life at least 1000 times longer than the half-life of a free digestive protein counterpart, wherein the water content of the hydrogel matrix is less than 10 weight percent, and wherein the amount of said at least one digestive protein is between about 0.2 to 5.0 dry weight percent of the hydrogel matrix.

2. The bioactive composition of claim 1 wherein the digestive protein remains biologically active after exposure to a temperature up to 110° Celsius.

3. The bioactive composition of claim 1 wherein the protein is selected from the digestive group consisting of protease, amylase, cellulose, lipase, peroxidase, tyrosinase, glycosidase, nuclease, aldolase, phosphatase, sufatase, dehydrogenase, and lysozyme and combinations thereof.

4. The bioactive composition of claim 1 further comprising a biochemically active agent selected from the group consisting of antibody, nucleic acid, fatty acid, hormone, vitamin, mineral, structural protein, enzymes, and therapeutic agents including histamine blockers and heparin.

5. The bioactive composition of claim 1, wherein the at least one digestive protein has a half-life time greater than 300 days when exposed to dry heat at a temperature of about 110 degrees Celsius.

* * * * *